US010918406B2

(12) United States Patent
Fiksen et al.

(10) Patent No.: US 10,918,406 B2
(45) Date of Patent: *Feb. 16, 2021

(54) SURGICAL APPARATUS WITH JAW FORCE LIMITER

(71) Applicant: Gyrus ACMI, Inc., Southborough, MA (US)

(72) Inventors: Christian J. Fiksen, Maple Grove, MN (US); Eric J. Boone, Saint Michael, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/800,544

(22) Filed: Feb. 25, 2020

(65) Prior Publication Data

US 2020/0187969 A1     Jun. 18, 2020

Related U.S. Application Data

(63) Continuation of application No. 16/434,859, filed on Jun. 7, 2019, now Pat. No. 10,610,248, which is a
(Continued)

(51) Int. Cl.
*A61B 17/29* (2006.01)
*A61B 18/14* (2006.01)
(Continued)

(52) U.S. Cl.
CPC .......... *A61B 17/29* (2013.01); *A61B 17/2909* (2013.01); *A61B 18/1445* (2013.01);
(Continued)

(58) Field of Classification Search
CPC ................ A61B 17/29; A61B 17/2909; A61B 2017/2925; A61B 2017/2926; A61B 2017/2932; A61B 18/1445; A61B 18/12; A61B 18/1442; A61B 90/03; A61B 2090/065; A61B 2090/034; A61B 2018/00607; A61B 2018/0063; A61B 2018/126; A61B 2018/00595
(Continued)

(56) References Cited

U.S. PATENT DOCUMENTS 5,683,412 A * 11/1997 Scarfone ................ A61B 17/29
606/205

* cited by examiner

*Primary Examiner* — Ronald Hupczey, Jr.
*Assistant Examiner* — Christine A Dedoulis
(74) *Attorney, Agent, or Firm* — Schwegman Lundberg & Woessner, P.A.

(57) ABSTRACT

A forceps includes a first jaw member, a second jaw member, a drive rod assembly and a moveable handle attached to a fixed handle. The first jaw member and the second jaw member are in opposing relation relative to one another, and at least one of the first jaw member and the second jaw member is relatively movable from a first open position to a second clamping position when the first jaw member and the second jaw member cooperate to grasp tissue therebetween. Moving the moveable handle relative to the fixed handle moves the drive rod assembly for imparting movement of at least one of the first jaw member and the second jaw member from the first position and the second position. The moveable handle has an actuator with a lost motion connection between the first and second jaw members and the actuator.

8 Claims, 8 Drawing Sheets

Related U.S. Application Data continuation of application No. 15/182,193, filed on Jun. 14, 2016, now Pat. No. 10,349,963.

(51) Int. Cl.
*A61B 90/00* (2016.01)
*A61B 18/00* (2006.01)

(52) U.S. Cl.
CPC ...... *A61B 90/03* (2016.02); *A61B 2017/2925* (2013.01); *A61B 2017/2926* (2013.01); *A61B 2017/2932* (2013.01); *A61B 2018/0063* (2013.01); *A61B 2018/00607* (2013.01); *A61B 2090/034* (2016.02); *A61B 2090/065* (2016.02)

(58) Field of Classification Search
USPC .......................................................... 606/52
See application file for complete search history.

SURGICAL APPARATUS WITH JAW FORCE LIMITER

RELATED APPLICATION

This application is a continuation of U.S. patent application Ser. No. 16/434,859, filed on Jun. 7, 2019, which is a continuation of U.S. patent application Ser. No. 15/182,193, filed on Jun. 14, 2016, which issued as U.S. Pat. No. 10,349,963 on Jul. 16, 2019. The entire contents of the above application are incorporated herein by reference.

FIELD

The present disclosure relates to a forceps. More specifically, the present disclosure relates to a forceps with jaw force limiter.

BACKGROUND

The statements in this section merely provide background information related to the present disclosure and may not constitute prior art.

Generally forceps may be utilized for laparoscopic surgery. The forceps may be employed to control delicate movements inside a patient and may include an end effector assembly with a pair of opposed resilient jaws that are closed against each other to grip tissue. Further, the forceps may utilize electrical energy that is delivered to the pair of opposed resilient jaws to coagulate or gut the tissue. Such devices, however, may produce high jaw forces to compress the tissue and, in some circumstances, high jaw forces to open the jaws. These high jaw forces can result in breakage of the end effector assembly.

Accordingly, there is a need in the art for forceps with a force limiting mechanism that prevents clamping forces imparted by the forceps' end effector from exceeding a predetermined amount of force to prevent breakage of the end effector.

SUMMARY

The present invention provides a forceps with a jaw force limiter. Accordingly, pursuant to one aspect of the present invention, a forceps includes a first jaw member, a second jaw member, a drive rod assembly and a moveable handle attached to a fixed handle. The first jaw member and the second jaw member are in opposing relation relative to one another, and at least one of the first jaw member and the second jaw member is relatively movable from a first open position when the first jaw member and the second jaw member are disposed in spaced relation relative to one another to a second clamping position when the first jaw member and the second jaw member cooperate to grasp tissue therebetween. Moving the moveable handle relative to the fixed handle moves the drive rod assembly for imparting movement of at least one of the first jaw member and the second jaw member from the first position and the second position. The moveable handle has an actuator with a lost motion connection between the first and second jaw members and the actuator. The lost motion connection includes a yoke and a drive shuttle. The yoke includes flanges and the drive shuttle is configured so that if a force imparted on the drive rod assembly exceeds a predetermined amount of force, the flanges of the yoke deflect outwardly to allow relative axial motion between the yoke and the shuttle, which allows relative movement between the moveable handle and the fixed handle without the first jaw member moving relative to the second jaw member.

The foregoing aspect of the present invention can be further characterized by one or any combination of the features described herein, such as: at least one of the yoke and the shuttle has a tapered surface that enables the at least one of the yoke and the shuttle to disengage from the other of the yoke and the shuttle; the at least one of the yoke and the shuttle has tapered surfaces on the front and the back of the at least one of the yoke and the shuttle that enables the at least one of the yoke and the shuttle to disengage from the other of the yoke and the shuttle; the drive rod assembly moves at least one of the first jaw member and the second jaw member towards the second clamping position as the moveable handle is moved towards the fixed handle; the lost motion connection allows the moveable handle to move away from the fixed handle without the first jaw member moving relative to the second jaw member so that the first jaw member and the second jaw member do not move towards the first open position when the moveable handle moves away from the fixed handle; the lost motion connection allows the moveable handle to move towards the fixed handle without the first jaw member moving relative to the second jaw member so that the first jaw member and the second jaw member do not move towards the second clamping position when the moveable handle moves towards the fixed handle; the first jaw member and the second jaw member each includes a sealing surfaces, each sealing surface being configured to connect to a source of electrosurgical energy; and the source generates electrosurgical energy to coagulate tissue grasped between the first jaw member and the second jaw member.

Accordingly, pursuant to another aspect of the present invention, a forceps includes a first jaw member, a second jaw member, a driver rod assembly, a moveable handle attached to a fixed handle, and a restorative member that provides a biasing force that biases the moveable handle away from the fixed handle. The first jaw member and the second jaw member are in opposing relation relative to one another, and the first jaw member and the second jaw member are relatively movable from a first open position when the first jaw member and the second jaw member are disposed in spaced relation relative to one another to a second clamping position when the first jaw member and the second jaw member cooperate to grasp tissue therebetween. Moving the moveable handle relative to the fixed handle moves the drive rod assembly for imparting movement of the first jaw member and the second jaw member between a first position and the second position. The moveable handle has an actuator with a lost motion connection between the first and second jaw members and the actuator. The lost motion connection is configured so that if a force imparted on the drive rod assembly exceeds a predetermined amount of force, the lost motion connection allows the movable handle to return away from the fixed handle to maintain the first jaw member and the second jaw member in the second clamped position.

The foregoing aspect of the present invention can be further characterized by one or any combination of the features described herein, such as: the lost motion connection includes a yoke on the end of the moveable handle and a drive shuttle, the yoke including flanges and the drive shuttle being configured so that if a force imparted on the drive rod assembly exceeds a predetermined amount of force, the flanges of the yoke deflect outwardly to allow relative axial motion between the yoke and the shuttle, which allows relative movement between the moveable handle and the fixed handle without the first jaw member moving relative to the second jaw member; at least one of the yoke and the shuttle has a tapered surface that enables the at least one of the yoke and the shuttle to disengage from the other of the yoke and the shuttle; the at least one of the yoke and the shuttle has tapered surfaces on the front and the back of the at least one of the yoke and the shuttle that enables the at least one of the yoke and the shuttle to disengage from the other of the yoke and the shuttle; the drive rod assembly moves at least one of the first jaw member and the second jaw member towards the second clamping position as the moveable handle is moved towards the fixed handle; the lost motion connection allows the moveable handle to move away from the fixed handle without the first jaw member moving relative to the second jaw member so that the first jaw member and the second jaw member do not move towards the first open position when the moveable handle moves away from the fixed handle; the lost motion connection allows the moveable handle to move towards the fixed handle without the first jaw member moving relative to the second jaw member so that the first jaw member and the second jaw member do not move towards the second clamping position when the moveable handle moves towards the fixed handle; the first jaw member and the second jaw member each includes a sealing surfaces, each sealing surface being configured to connect to a source of electrosurgical energy; and the source generates electrosurgical energy to coagulate tissue grasped between the first jaw member and the second jaw member.

Accordingly, pursuant to yet another aspect of the present invention, a method of using forceps includes one or more of the following steps: moving a moveable handle relative to a fixed handle of the forceps to grasp tissue between a first jaw member and a second jaw member of the forceps, the first jaw member and the second jaw member being in opposing relation relative to one another, the first jaw member and the second jaw member being relatively movable from a first open position when the first jaw member and the second jaw member are disposed in spaced relation relative to one another to a second clamping position when the first jaw member and the second jaw member cooperate to grasp tissue therebetween, and moving the moveable handle relative to the fixed handle to release the tissue. Moving the moveable handle relative to the fixed handle moves a drive rod assembly for imparting movement of the first jaw member and the second jaw member between the first position and the second position. The moveable handle has an actuator with a lost motion connection between the first and second jaw members and the actuator. The lost motion connection includes a yoke on the end of the moveable handle and a drive shuttle. The yoke includes flanges and the drive shuttle is configured so that if a force imparted on the drive rod assembly exceeds a predetermined amount of force, the flanges of the yoke deflect outwardly to allow relative axial motion between the yoke and the shuttle, which allows relative movement between the moveable handle and the fixed handle without the first jaw member moving relative to the second jaw member.

The method of using the forceps may be further characterized by one or any combination of the following features: at least one of the yoke and the shuttle has a tapered surface that enables the at least one of the yoke and the shuttle to disengage from the other of the yoke and the shuttle; the at least one of the yoke and the shuttle has tapered surfaces on the front and the back of the at least one of the yoke and the shuttle that enables the at least one of the yoke and the shuttle to disengage from the other of the yoke and the shuttle; the drive rod assembly moves the first jaw member towards the second jaw member as the moveable handle is moved towards the fixed handle; the lost motion connection allows the moveable handle to move away from the fixed handle without the first jaw member moving relative to the second jaw member so that the first jaw member and the second jaw member do not move towards the first open position when the moveable handle moves away from the fixed handle; the lost motion connection allows the moveable handle to move towards the fixed handle without the first jaw member moving relative to the second jaw member so that the first jaw member and the second jaw member do not move towards the second clamping position when the moveable handle moves towards the fixed handle; the first jaw member and the second jaw member each includes a sealing surfaces, each sealing surface being configured to connect to a source of electrosurgical energy; and the source generates energy to coagulate tissue grasped between the first jaw member and the second jaw member.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
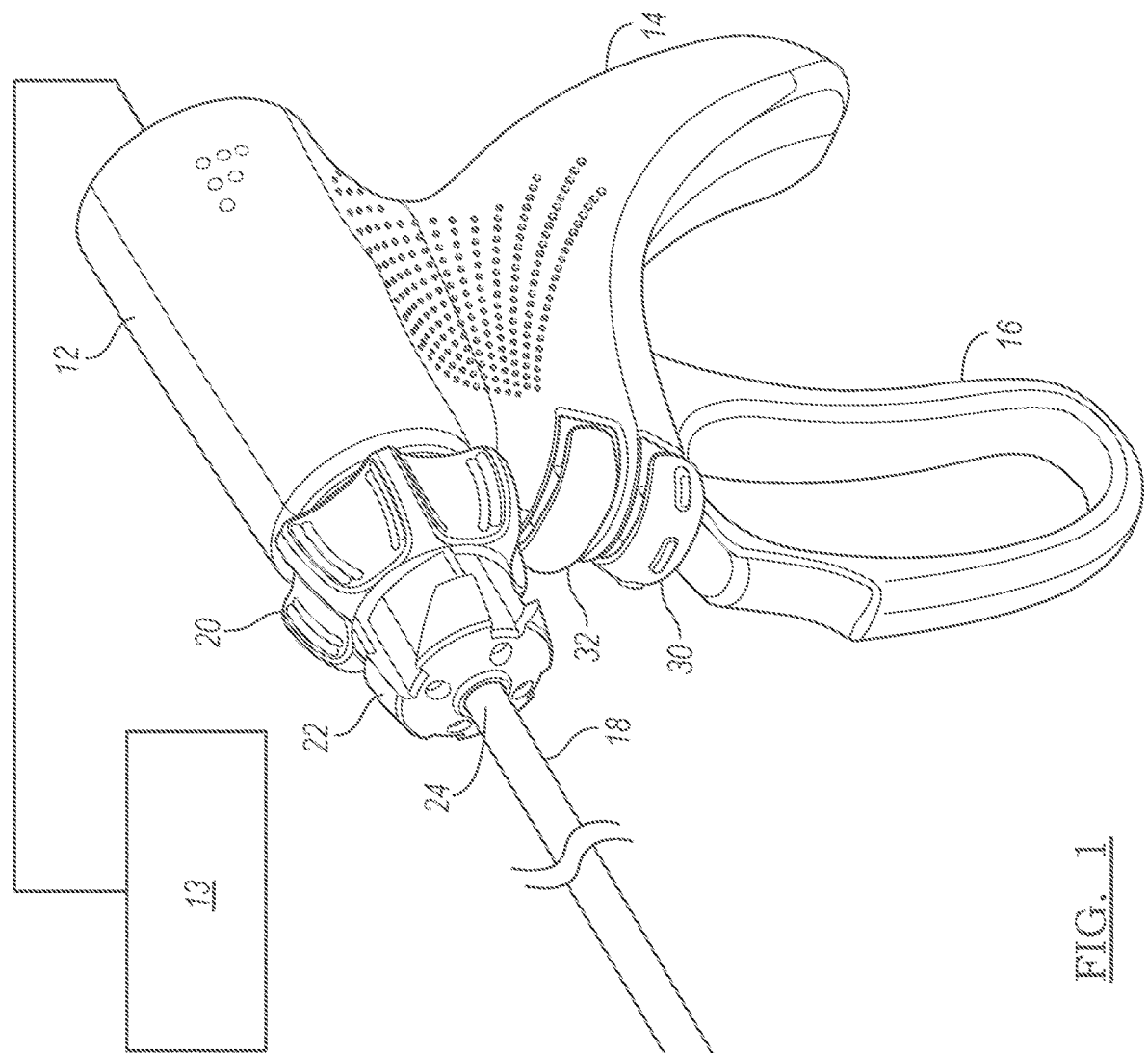
FIG. 1 is a perspective view of a forceps in accordance with the principles of the present invention.

With reference to FIG. 1, an instrument embodying the principles of the present invention is illustrated therein and designated at 10. In certain configurations, the instrument 10 is a bipolar forceps used to seal, coagulate, or cut the tissue. The instrument 10 may be employed during surgery to grip a feature of interest including a part of a body, an anatomical feature, tissue, veins, arteries, or a combination thereof.

Current may be passed through the forceps 10 so that the forceps are used for electrosurgery. For example, a therapy current may be passed from one jaw to a second jaw when tissue is located within the jaw and the therapy current may coagulate blood, cauterize, cut, or a combination thereof. The forceps 10 may generally include one or more working assemblies and sufficient controls to work the one or more assemblies. The forceps 10 may include parts employed to perform the recited functions and may include generally, a stylet (e.g., a tubular member, a hollow tube, or an assembly of tubes), a hand piece, one or more operable mechanisms used to actuate the stylet, or a combination thereof. The hand piece may be an assembly of parts or housing structures capable of forming a hand piece structure with a cavity. Note that the present invention is not limited to laparoscopic procedures. That is, the below described jaws can be employed with any type of medical device that clamps onto tissue.

Turning now to FIG. 1, the forceps 10 includes a handpiece 12 and a sheath member 18 with a proximal portion 24 connected to the handpiece 12 with a connector knob 22. In various arrangements, the sheath member 18 can be an outer pipe with a heat shrink. An end effector unit 28 extends from a distal portion 26 of the sheath member 18. The handpiece 12 includes a moveable handle 16 configured to move relative to a fixed handle 14. The handpiece 12 also includes a first switch button 32 and a second switch button 30.

Figure 2:
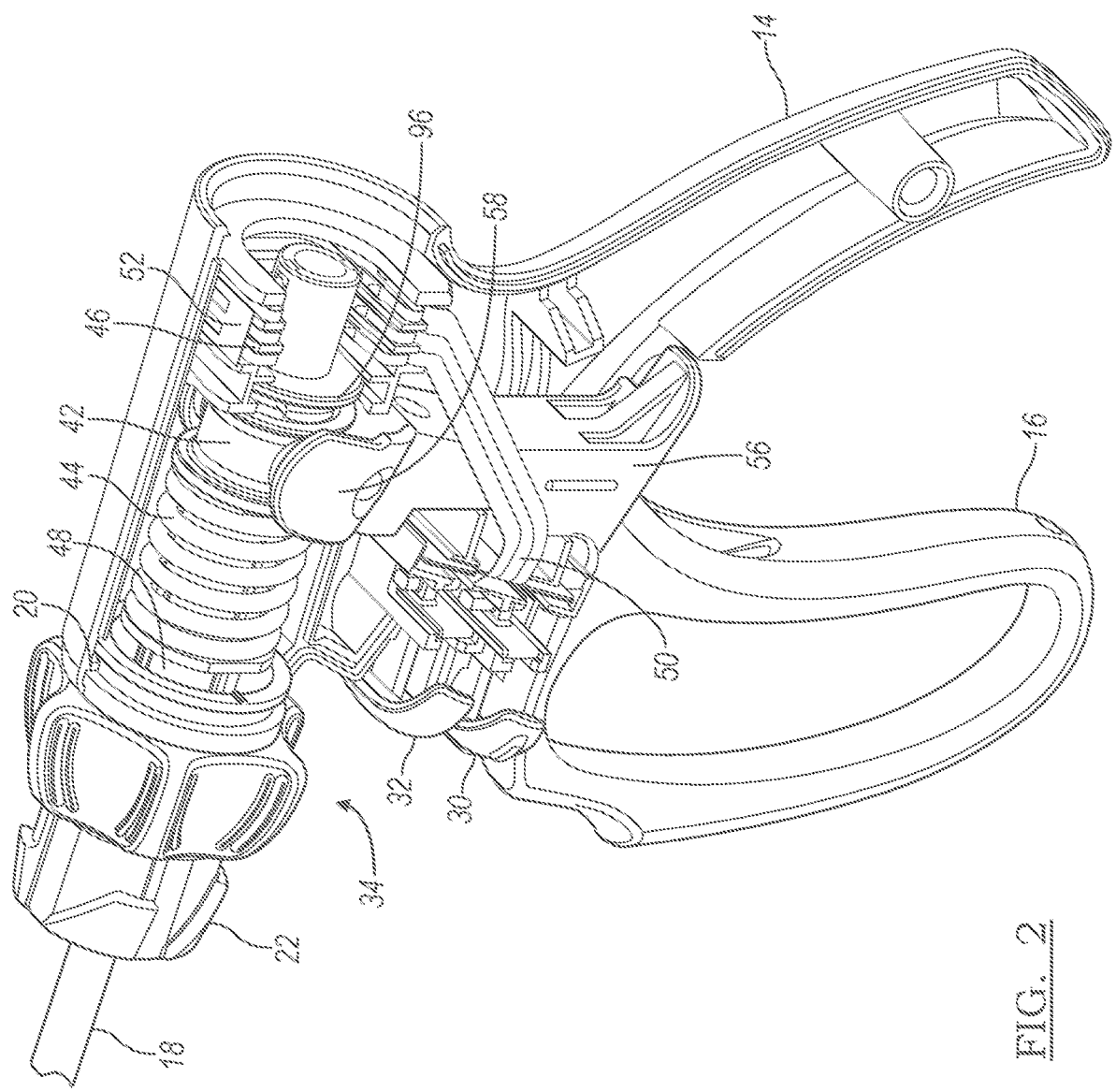
FIG. 2 is an interior view of the forceps shown in FIG. 1.
Figure 3:
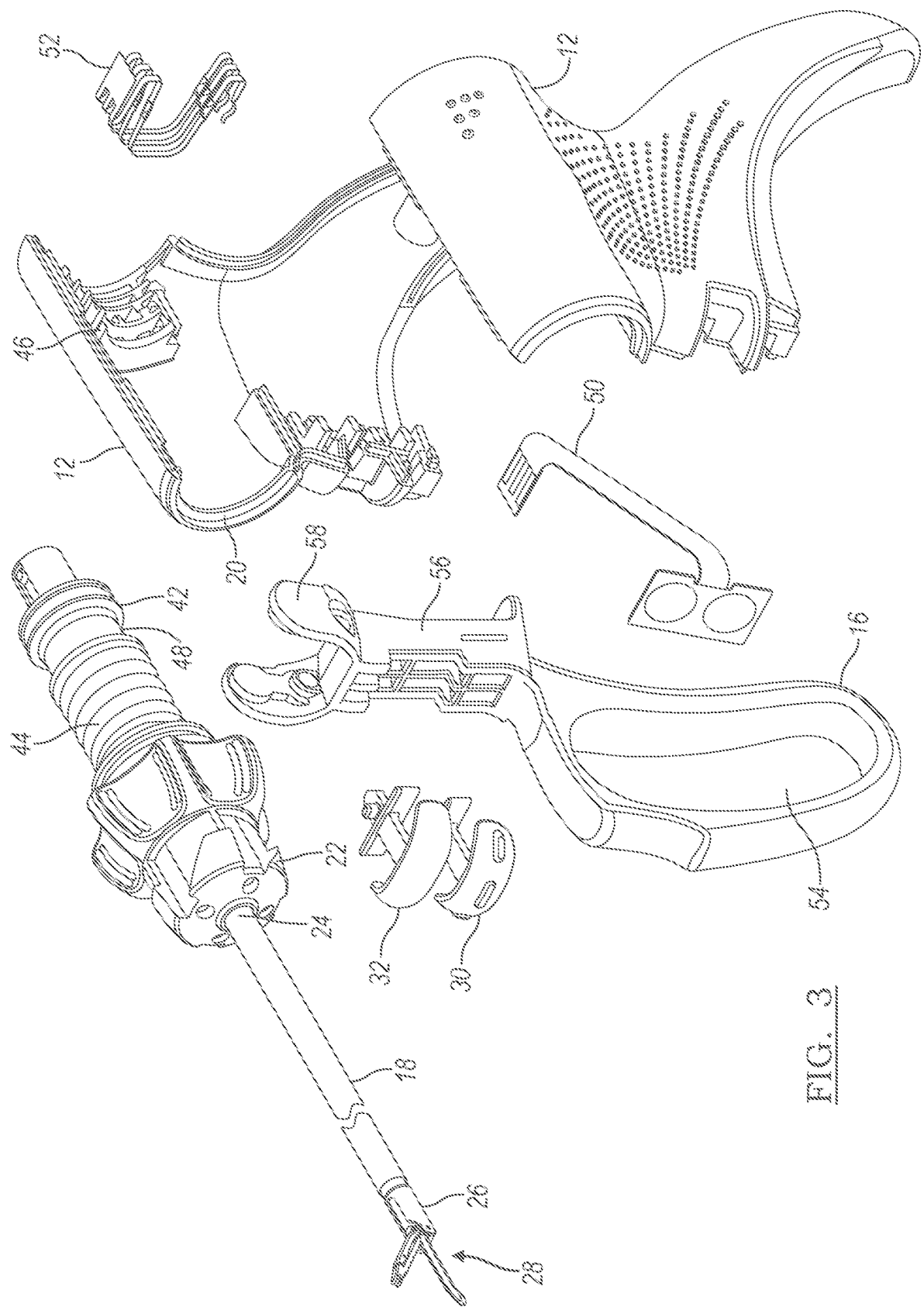
FIG. 3 is an expanded view of the forceps shown in FIG. 1.

Referring further to FIGS. 2 and 3, the forceps 10 includes a flexible circuit 50 that electrically communicates with the first and second switch buttons 30 and 32. The flexible circuit 50, in turn, electrically communicates with a contact switch circuit 52 that is electrically connected to an electrosurgical energy source 13. When the second switch button 30 is depressed, the energy source 13 is activated to supply energy to the end effector 28 to coagulate tissue grasped by the end effector 28. And when depressed, the first switch button 32 activates the electrosurgical energy source 13 to supply sufficient energy, electrosurgical or ultrasonic, to the end effector 28 to cut and seal tissue grasped by the end effector 28.

Figure 4:
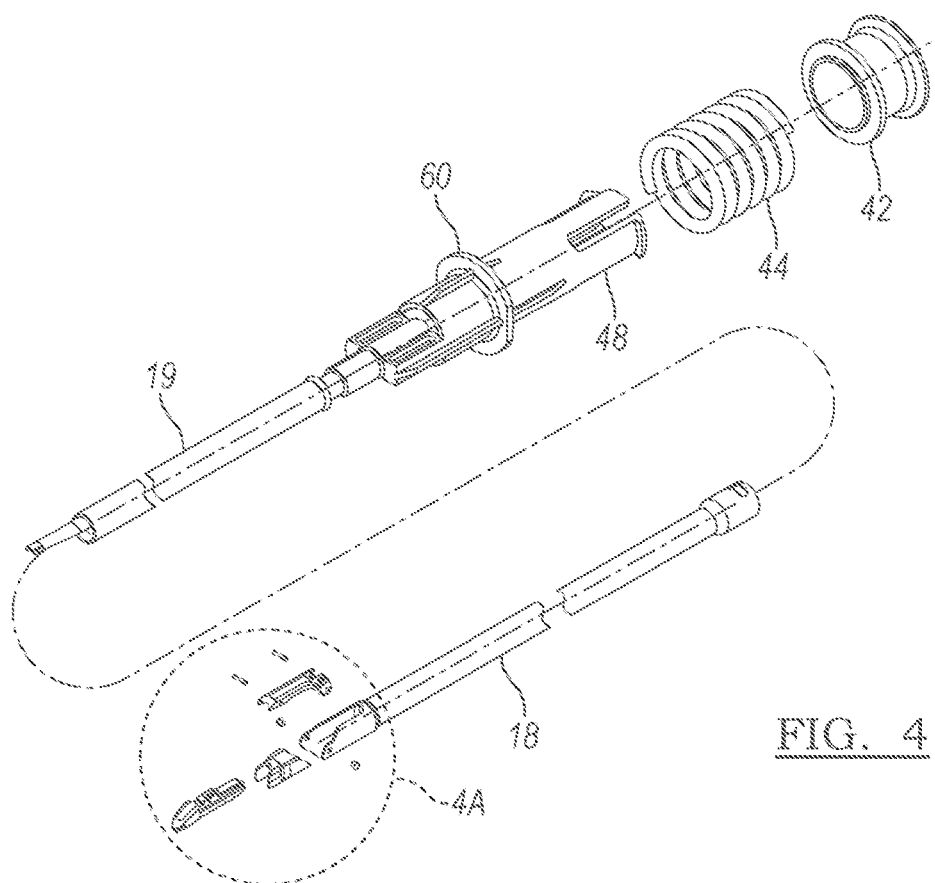
FIG. 4 is an expanded view of an upper jaw and slider sub-assembly for the forceps shown in FIG. 1.
Figure 4A:
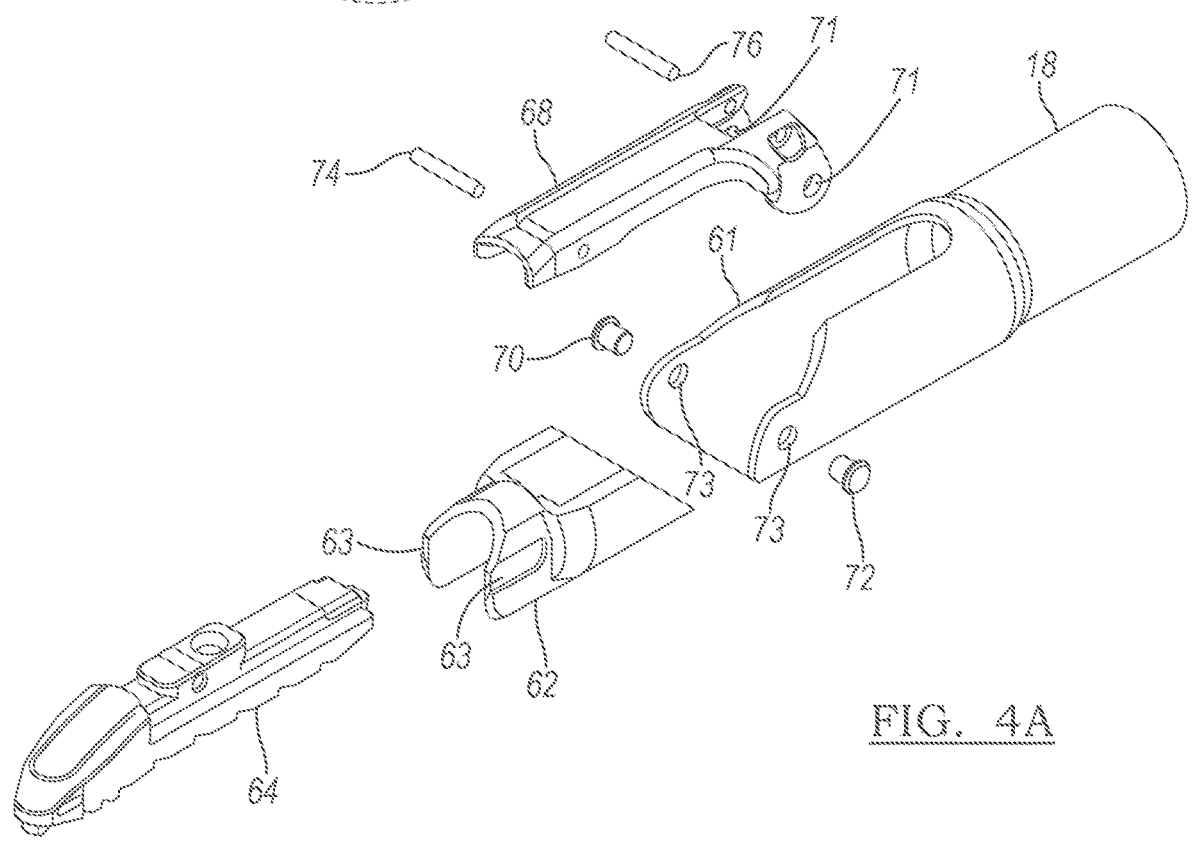
FIG. 4A is a close-up view of the region 4A shown in FIG. 4.
Figure 5:
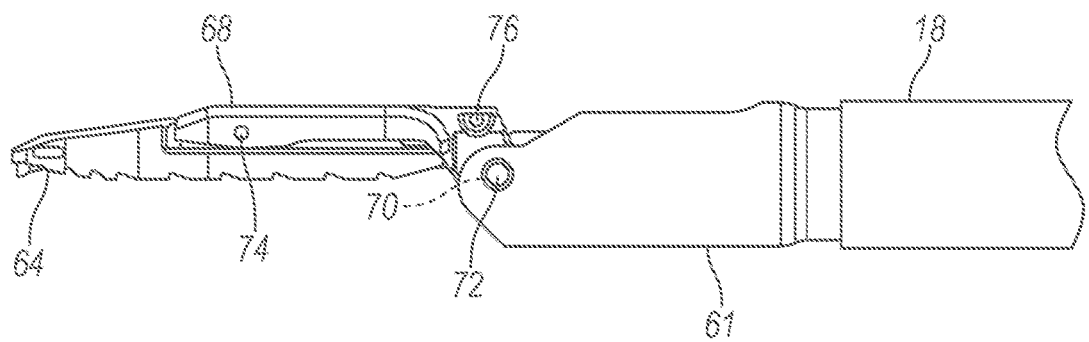
FIG. 5 is a side view of the upper jaw shown in FIG. 4.
Figure 6:
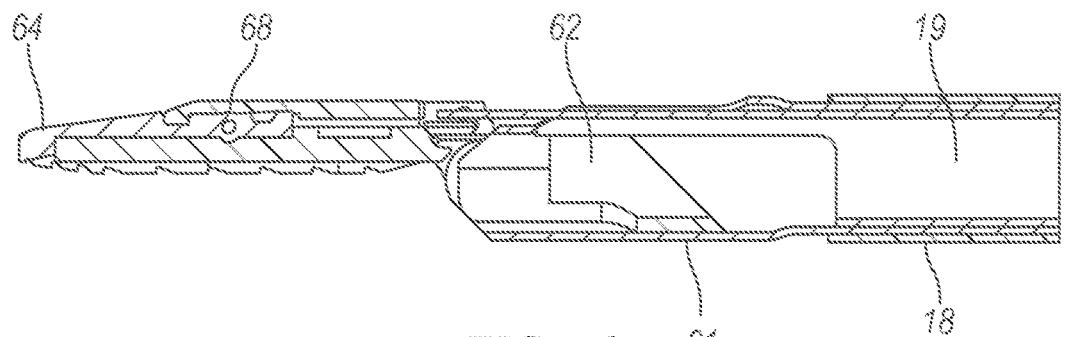
FIG. 6 is cross-sectional view of the upper shown in FIG. 5.

The forceps 10 includes an actuator 34 associated with the moveable handle 16. The actuator 34 includes a slider 48, a biasing member such as a spring 44 positioned about the slider 48, and a shuttle 42 also positioned about the slider 48. The moveable handle 16 includes an extension 56 with a yoke 58. The yoke 58 is engaged with the shuttle 42, and together the yoke 58 and the shuttle 42 form a lost motion connection, described in more detail below, between the actuator 34 and the end effector 28. Squeezing the moveable handle 16 towards the fixed handle 14 moves the shuttle 42 distally, that is, towards the end effector 28. Such movement of the shuttle 42 compresses the spring member 44 against an enlarged flange 60 (see, for example, FIG. 4), so that the slider 48 moves distally as well.

Referring also to FIGS. 4, 4A, 5 and 6, the slider 48 is connected to a tubular member or inner pipe 19 that is disposed inside the sheath member 18 and is configured to enable the tubular member 19 to reciprocate within the sheath member 18, and, hence, operates as a drive rod assembly to open the end effector 28 and to close the end effector 28 to a clamping position. The drive rod can be a hollow shaft; hence, the drive rod assembly can operate as a push tube assembly or driver tube assembly. The sheath member 18 includes a connector 61, and a holder 62 resides within the connector 61. The end effector 28 includes a first jaw member such as the upper jaw member 68 attached to the connector 61 with a set of pins 70 and 72. More specifically, the set of pins 70 and 72 extend through a pair of holes 73 in the connector 61 and through pair of holes 71 of the upper jaw member 68. The inner ends of the pins 70 engage with respective slots 63 of the holder 62. A pin 76 engages the end of the tubular member 19 to the upper jaw member 68. Accordingly, movement of the tubular member 19 distally causes the tubular member 19 to push against the pin 76, which, in turn, pushes against the upper jaw member 68 to pivot the upper jaw member 68 downwards about the pins 70 and 72 to the clamping position. The holder 62 remains stationary within the sheath 18 and helps keep a distal member 86 (FIG. 7) centered in the tubular member 19. The holder 62 is made of an insulating material, such as, for example, a plastic, to ensure that the distal member 86 and the tubular member 19 are electrically isolated from each other. An electrode 64 is attached to the bottom of the upper jaw member 68 with a pin or shaft 74 and is electrically connected to the energy source 13 such that the electrode 64 functions as a sealing surface.

Figure 7:
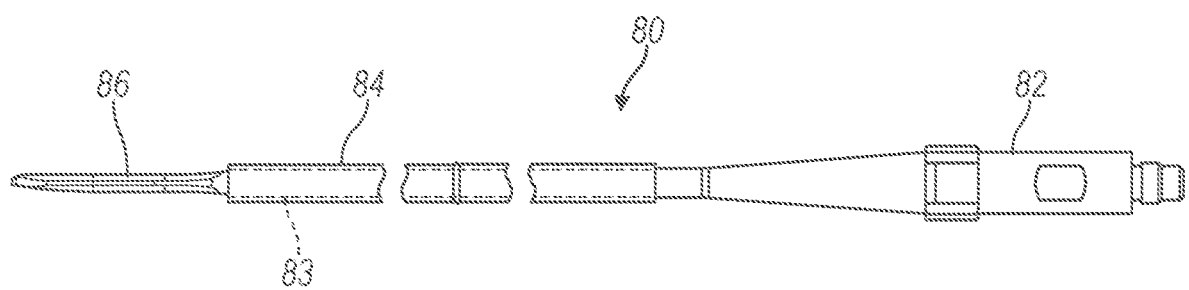
FIG. 7 is a side view of a probe sub-assembly.

Turning now to FIG. 7, the forceps 10 further includes a sub-assembly member 80 with an inner shaft 83 housed within an inner sheath 84. The inner shaft 83 is connected to an enlarged proximal end 82 and to the distal member 86 at the distal end of the shaft 83. The distal member 86 can be a probe, a second jaw member, or both a probe and a second jaw member. The distal member 86, in various arrangements, receives ultrasonic energy delivered by the source 13, such that the distal member functions as a cutting element. The distal member 86 can function as an electrode with a sealing surface. Hence, if both the upper jaw member 68 includes an electrode 64 and the distal member 86 includes an electrode, the end effector 28 operates as opposed electrodes of a bipolar forceps.

Figure 8A:
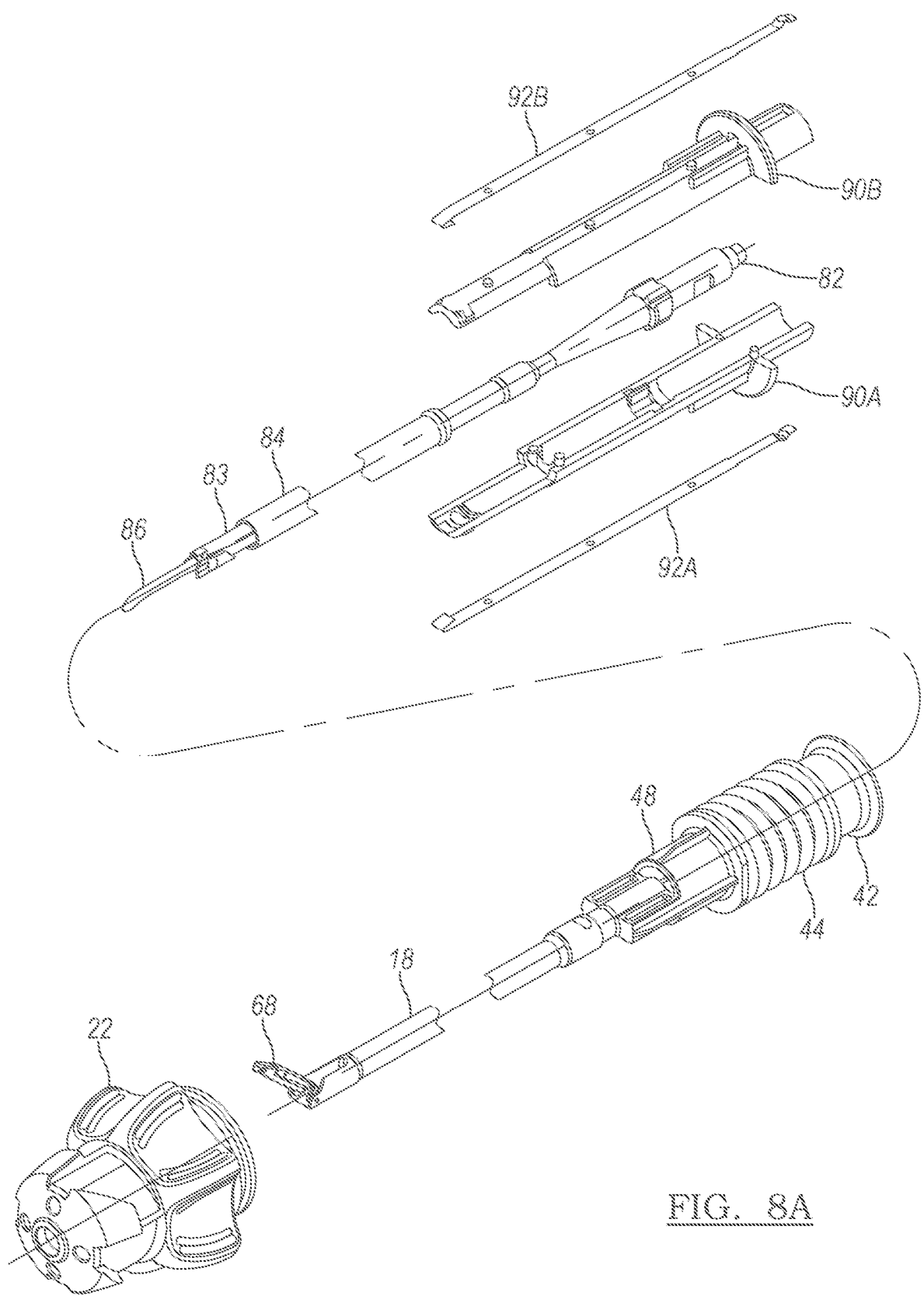
FIG. 8A is an expanded view of the probe sub-assembly shown in FIG. 7 combined with a connector sub-assembly.

As shown in FIG. 8A, the enlarged proximal end 82 is housed in a two piece probe holder 90A and 90B. Elongated electrical contacts 92A and 92B are positioned on the outside of the probe holders 90A and 90B and are electrically connected to the electrical source 13. As further shown in FIG. 8A, the inner shaft 83 and the inner sheath 84 are positioned within the tubular member 19 and are configure to allow the tubular member 19 to reciprocate over the inner sheath 84.

Figure 8B:
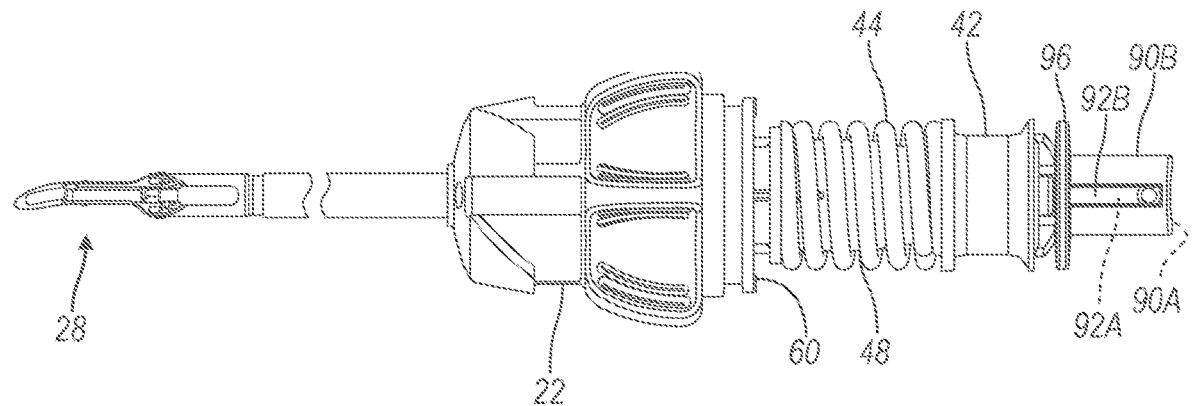
FIG. 8B is a side view of the probe sub-assembly and connector sub-assembly shown in FIG. 8A.
Figure 8C:
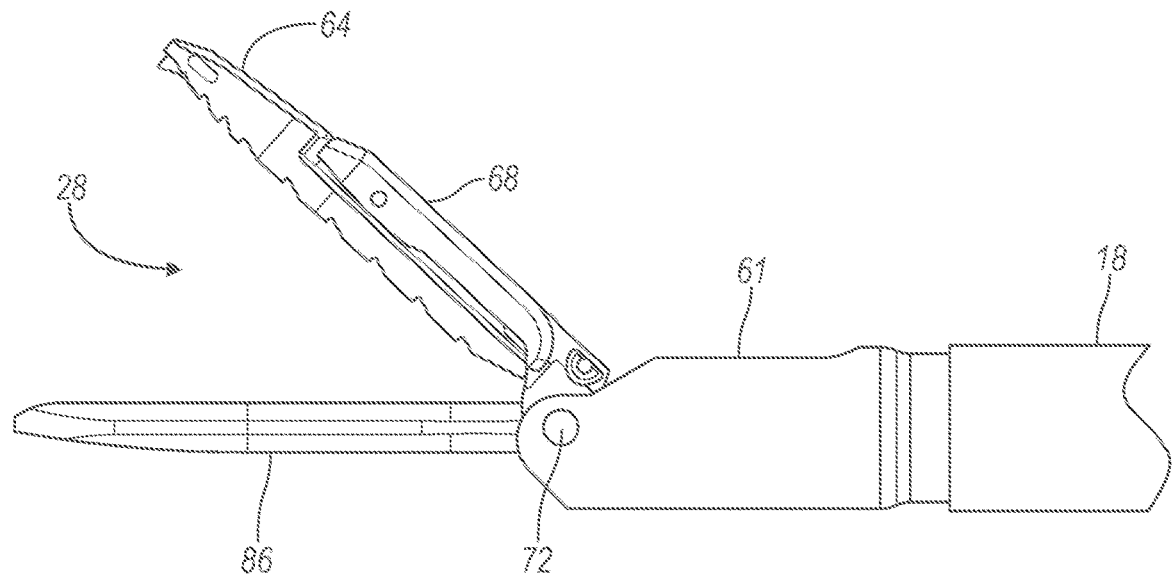
FIG. 8C is close-up side view of the upper jaw and the probe.

Referring also to FIG. 8B, the two-piece probe holder 90A and 90B includes an enlarged flange 96 that engages with one of a set of ribs 46 (see, for example, FIG. 2) inside the handpiece 12. Accordingly, the probe sub-assembly member 80 remains stationary within the handpiece 12 while the slider 48, the spring 44 and the shuttle 42 are able to translate relative to the sub-assembly 80.

Figure 9:
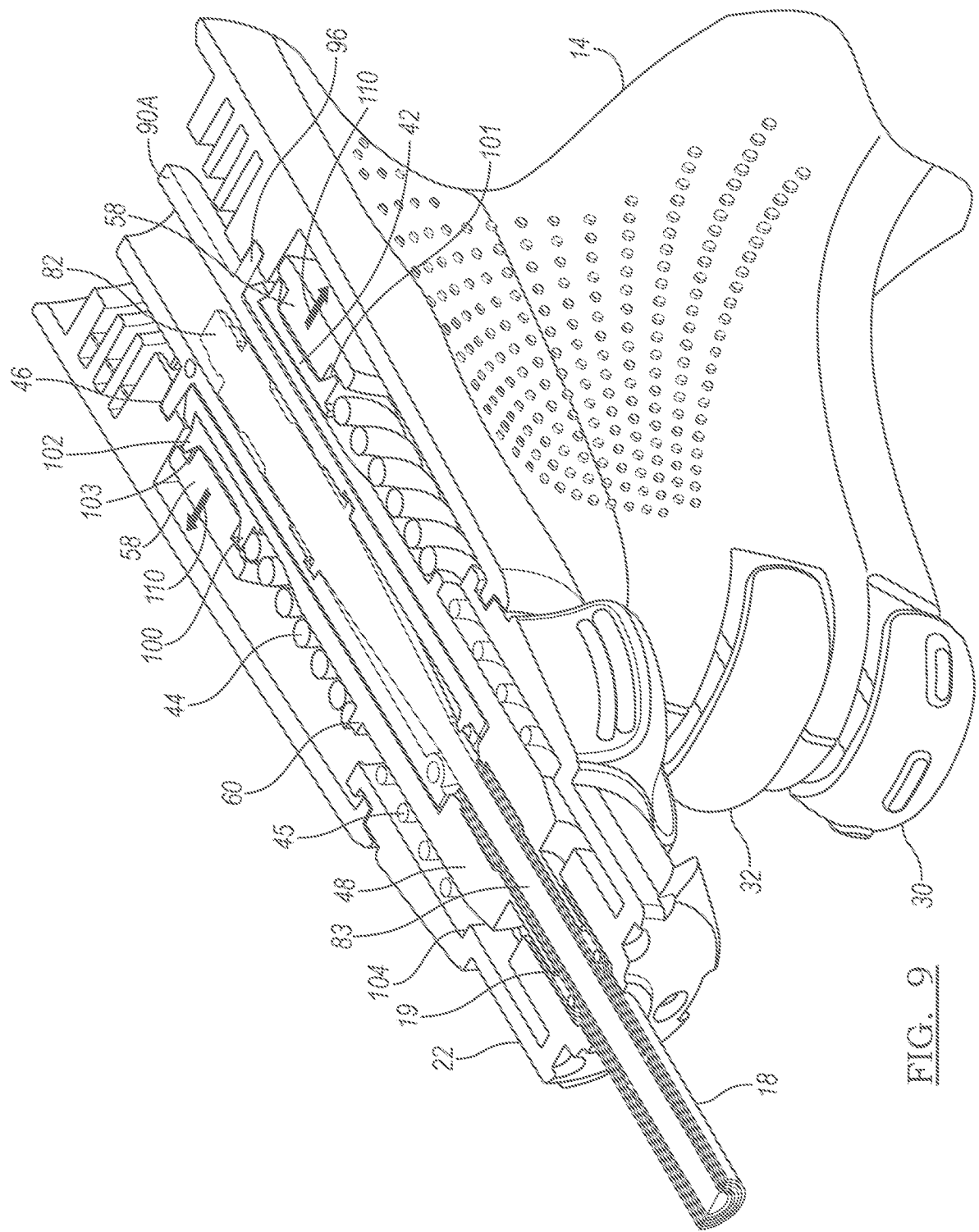
FIG. 9 is a cross-sectional view of a handpiece for the forceps shown in FIG. 1.

Referring now to FIG. 9, the slider 48 includes a flange 60. A second biasing member such as a spring 45 is positioned between the flange 60 and a surface 104 of a reduced diameter region of the connector knob 22. Thus, movement of the moveable handle 16 towards the fixed handle 14 causes the yoke 58 to move distally. Since the yoke 58 is engaged with the shuttle 42, distal movement of the yoke 58 pushes the shuttle 42, which compresses the spring 44 against the slider flange 60, which, in turn, moves the slider 48 distally. Distal movement of the slider 48 compresses the spring 45 between the surface 104 and the flange 60. Since the tubular member 19 is connected to the slider 48, movement of the slider 48 results in movement of the tubular member 19 within the sheath 18 and over the inner sheath 84. And, as described earlier, since the tubular member 19 is engaged with the pin 76, distal movement of the tubular member 19 results in distal movement of the pin 76, which causes the upper jaw member 68 to pivot downwards to the closed clamping position. To open the end effector 28, the moveable handle 16 is moved away from the fixed handle 14. More specifically, movement of the handle 16 away from the fixed handle 14 results in the shuttle 42 to move proximally, which allows the spring 44 to expand to lessen the compressive forces on the flange 60 of the slider 48. As a result, the spring 45 is able to expand as well to push against the flange 60, which results in proximal movement of the slider 48. Since, as discussed above, the slider 48 is connected to the end effector 28, proximal movement of the slider 48 results in the upper jaw member to pivot upwards to the open position. Further note that in certain arrangements of the forceps 10, the spring 45 acts as a restorative member that provides a biasing force on the moveable handle 16 away from the fixed handle 14. Specifically, the lost motion connection, that is, the yoke 58 and the shuttle 42, transfers the biasing force to the moveable handle 16 to return the moveable handle 16 away from the fixed handle 14 to maintain the upper jaw member 68 and the distal member 86 in the closed clamping position.

During use of the forceps 10, excessive clamping forces imparted on the end effector 28 may result in breakage of the end effector 28. In particular, such forces can cause the pins 70 and 72 or 74 and 76 to break away or disengage from the upper clamping member 68. The lost motion connection described previously prevents such breakage from happening. The shuttle 42 includes a distal flange 100 and a proximal flange 102. The distal flange 100 allows the yoke 58 to snap over the shuttle 42, as indicated by the arrows 110, before the clamping forces of the end effector 28 become excessive as the moveable handle 16 is squeezed towards the fixed handle 14. That is, if the clamping force imparted by the drive rod assembly exceeds a predetermined amount of force, the distal flange 100 of the yoke 58 deflects outwardly to allow enable relative axial movement between the yoke 58 and the shuttle 42, which allows relative movement between the moveable handle 16 and the fixed handle 14 without the upper jaw member 68 moving relative to the distal member 86.

Similarly, excessive forces may occur while opening the end effector 28 as the moveable handle 16 is moved away from the fixed handle 14. Hence, if the opening force imparted by the drive rod assembly exceeds a predetermined amount of force, the proximal flange 102 of the yoke 58 deflects outwardly to enable the yoke 58 to snap over the shuttle 42, which again allows relative axial movement between the yoke 58 and the shuttle 42 while allowing relative movement between the moveable handle 16 and the fixed handle 14 without the upper jaw member 68 moving relative to the distal member 86.

In sum, the lost motion connection allows the moveable handle 16 to move away from the fixed handle 14 without the upper jaw member 68 moving relative to the distal member 86 so that the upper jaw member 68 and the distal member 86 do not move towards the open position when the moveable handle 16 moves away from the fixed handle 14. Further, the lost motion connection allows the moveable handle 16 to move towards the fixed handle 14 without the upper jaw member 68 moving relative to the distal member 86 so that the upper jaw member 68 and the distal member 86 do not move towards the closed clamping position when the moveable handle 16 moves towards the fixed handle 14. In certain arrangements, either flange 100 or 102 or both of them can include tapered surfaces 101 and 103, respectively, as shown in FIG. 9 to further enhance disengagement between the yoke 58 and the shuttle 42 to prevent the drive rod assembly from imparting excessive forces on the end effector 28.

The description of the invention is merely exemplary in nature and variations that do not depart from the gist of the invention are intended to be within the scope of the invention. Such variations are not to be regarded as a departure from the spirit and scope of the invention.

What is claimed is:

1. A forceps comprising:
   a first jaw member;
   a second jaw member, the first jaw member and the second jaw member being in opposing relation relative to one another, the first jaw member and the second jaw member being relatively movable from a first open position when the first jaw member and the second jaw member are disposed in spaced relation relative to one another to a second clamping position when the first jaw member and the second jaw member cooperate to grasp tissue therebetween;
   a drive rod assembly; and
   a moveable handle attached to a fixed handle, the moveable handle configured to move relative to the fixed handle to move the drive rod assembly for imparting movement of the first jaw member and the second jaw member between the first position and the second position, the moveable handle having an actuator with a lost motion connection between the first and second jaw members and the actuator,
   wherein the lost motion connection is configured so that if a force imparted on the drive rod assembly exceeds a predetermined amount of force, the lost motion connection allows the movable handle to return away from the fixed handle to maintain the first jaw member and the second jaw member in the second clamped position, and
   wherein the lost motion connection allows the moveable handle to move towards the fixed handle without the first jaw member moving relative to the second jaw member so that the first jaw member and the second jaw member do not move towards the second clamping position when the moveable handle moves towards the fixed handle.

2. The forceps of claim 1 wherein the lost motion connection includes a yoke on the end of the moveable handle and a drive shuttle, the yoke including flanges and the drive shuttle being configured so that if a force imparted on the drive rod assembly exceeds a predetermined amount of force, the flanges of the yoke deflect outwardly to allow relative axial motion between the yoke and the shuttle, which allows relative movement between the moveable handle and the fixed handle without the first jaw member moving relative to the second jaw member.

3. The forceps of claim 2 wherein at least one of the yoke and the shuttle has a tapered surface that enables the at least one of the yoke and the shuttle to disengage from the other of the yoke and the shuttle.

4. The forceps of claim 1 wherein the drive rod assembly moves at least one of the first jaw member and the second jaw member towards the second clamping position as the moveable handle is moved towards the fixed handle.

5. The forceps of claim 1 wherein the lost motion connection allows the moveable handle to move away from the fixed handle without the first jaw member moving relative to the second jaw member so that the first jaw member and the second jaw member do not move towards the first open position when the moveable handle moves away from the fixed handle.

6. The forceps of claim 1 wherein the lost motion connection allows the moveable handle to move away from the fixed handle without the first jaw member moving relative to the second jaw member so that the first jaw member and the second jaw member do not move towards the first open position when the moveable handle moves away from the fixed handle, and wherein the lost motion connection allows the moveable handle to move towards the fixed handle without the first jaw member moving relative to the second jaw member so that the first jaw member and the second jaw member do not move towards the second clamping position when the moveable handle moves towards the fixed handle.

7. The forceps of claim 1 wherein the first jaw member and the second jaw member each includes a sealing surface, each sealing surfaces being configured to connect to a source of electrosurgical energy.

8. The forceps of claim 7 wherein the source of electrosurgical energy is configured to generate electrosurgical energy to coagulate tissue grasped between the first jaw member and the second jaw member.

\* \* \* \* \*